(12) United States Patent
McWhorter

(10) Patent No.: US 6,571,636 B1
(45) Date of Patent: Jun. 3, 2003

(54) WHEEL-TYPE TRANSMIT/RECEIVE ULTRASONIC INSPECTION DEVICE WITH CONSTANT LENGTH INTERNAL LIQUID SOUNDPATH

(75) Inventor: Paul H. McWhorter, Pueblo, CO (US)

(73) Assignee: CF&I Steel, L.P., Pueblo, CO (US)

( * ) Notice: Subject to any disclaimer, the term of this patent is extended or adjusted under 35 U.S.C. 154(b) by 131 days.

(21) Appl. No.: 09/661,599

(22) Filed: Sep. 14, 2000

(51) Int. Cl.[7] .............................................. G01N 29/04
(52) U.S. Cl. .......................... 73/649; 73/636; 73/639; 73/644; 73/660
(58) Field of Search .......................... 73/649, 639, 641, 73/644, 660, 635, 636

(56) References Cited

U.S. PATENT DOCUMENTS

| | | | |
|---|---|---|---|
| 3,205,702 A | * 9/1965 | Joy | 73/639 |
| 4,165,648 A | 8/1979 | Pegano | 73/625 |
| 4,174,636 A | 11/1979 | Pegano | 73/636 |
| 4,202,216 A | * 5/1980 | Bull et al. | 73/639 |
| 4,398,421 A | 8/1983 | White | 73/597 |
| 4,437,332 A | 3/1984 | Pittaro | 73/597 |
| 4,472,974 A | * 9/1984 | Dickson et al. | 73/635 |
| 4,615,218 A | 10/1986 | Pegano | 73/639 |
| 4,763,526 A | 8/1988 | Pegano | 73/639 |
| 4,856,334 A | * 8/1989 | Shearer et al. | 73/588 |
| 5,419,196 A | * 3/1995 | Havira et al. | 73/636 |
| 5,880,370 A | * 3/1999 | Wachter et al. | 73/634 |
| 6,055,862 A | * 5/2000 | Martens | 73/632 |
| 6,138,515 A | * 10/2000 | Moufle et al. | 73/639 |
| 6,347,550 B1 | * 2/2002 | Kroening et al. | 73/598 |

\* cited by examiner

*Primary Examiner*—Hezron Williams
*Assistant Examiner*—Jacques Saint Surin
(74) *Attorney, Agent, or Firm*—Robert L. Harrington; Schwabe Williamson & Wyatt

(57) ABSTRACT

A wheel-type inspection device includes within the wheel structure a sensor head. The sensor head carries both ultrasonic transducers and a surface tracking structure maintained at fixed distance relative to the transducers. In operation, the surface tracking structure remains against the inner surface of the tire and thereby maintains a fixed distance between the transducers and the surface of the work piece under inspection. As a result, reflected sound energy analysis need not compensate for variations in distance between the transducers and the work piece because no such variations in distance occur under the disclosed device.

20 Claims, 9 Drawing Sheets

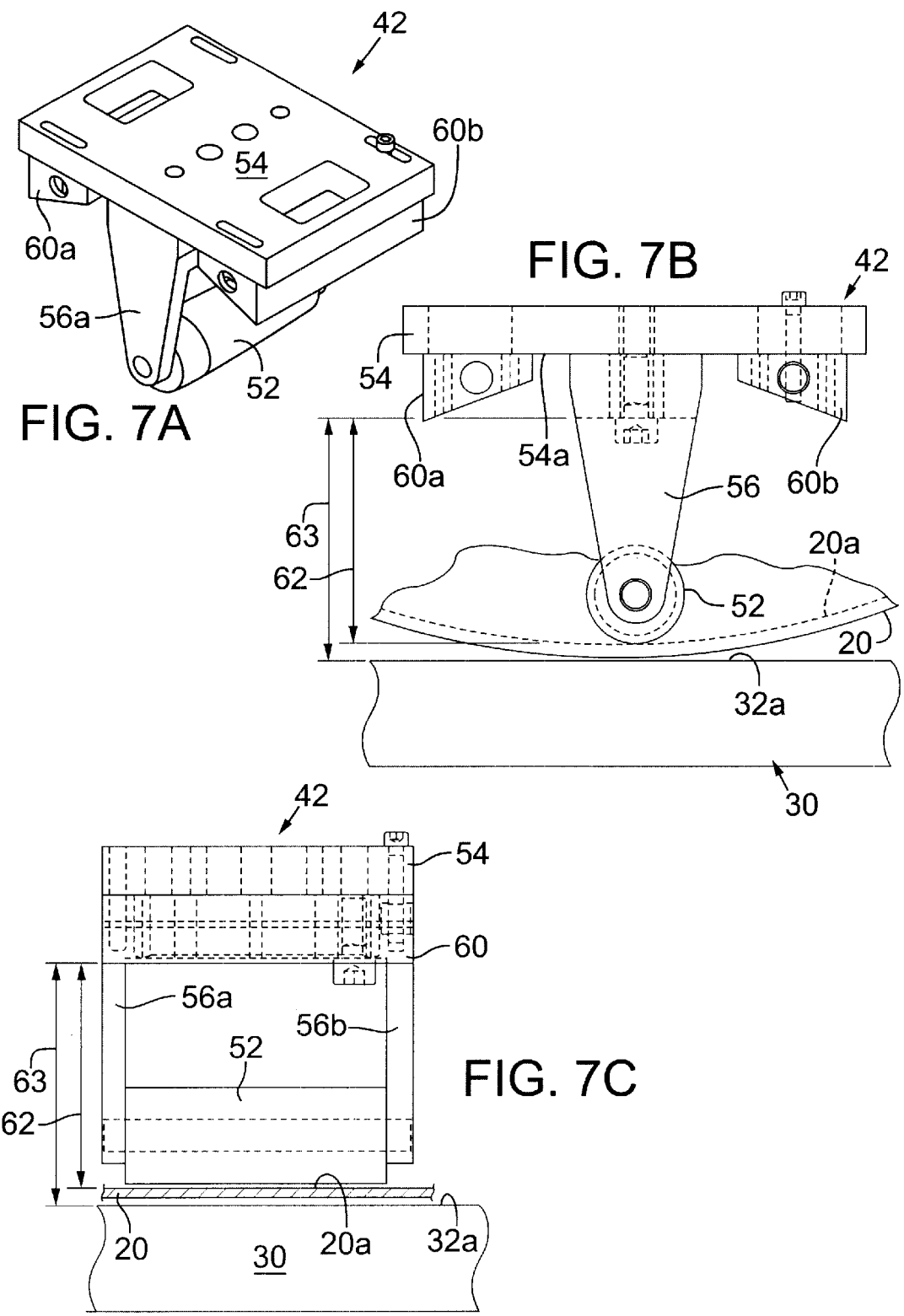

WHEEL-TYPE TRANSMIT/RECEIVE ULTRASONIC INSPECTION DEVICE WITH CONSTANT LENGTH INTERNAL LIQUID SOUNDPATH

BACKGROUND OF THE INVENTION

A wheel-type ultrasonic inspection device transmits ultrasonic sound waves into a work piece, e.g., a metallic piece, via an intervening liquid. The body of liquid serves as a carrier for the ultrasonic sound waves. The inspection device analyzes sound energy reflected back from the surface and from within the work piece to identify defects, e.g., cracks or pockets, therein. The inspection device includes a hollow wheel structure carrying therewithin the body of liquid and the ultrasonic transmitters/receivers. The liquid remains at the well, i.e., bottom, of the wheel as it rolls relative to the surface of the work piece. In a typical application, the inspection device as a whole remains stationary while the work piece moves therepast contacting the exterior of the wheel structure. The wheel structure thereby rotates by virtue of the work piece moving therepast. The ultrasonic transmitters/receivers, by appropriate mechanical mounting, remain directed downward toward the body of liquid and toward the surface of the work piece. In this manner, the device maintains the intervening liquid in place between the ultrasonic transmitters/receivers and the surface of the work piece under inspection. Reflected ultrasonic sound waves represent surface and internal conditions along the length of the work piece under inspection.

U.S. Pat. No. 4,615,218 entitled ULTRASONIC WHEEL PROBE WITH ACOUSTIC BARRIER issued Oct. 7, 1986 to D. Pagano discusses some history of wheel-type inspection devices and discloses a device having a vertically moveable acoustic barrier interposed between the ultrasonic transmitters/receivers. The barrier extends downward and into the body of liquid and bears against the inner surface of the tire. The acoustic barrier blocks "cross-talk" directly between the transmitters/receivers thereby making reflected sound energy, i.e., reflected from the surface or internal portions of the work piece, predominate sound energy available for analysis. A spring urges the acoustic barrier against inner surface of the tire, i.e., the barrier moves vertically relative to the hub of the device but remains held downward against the inner surface of the tire. As the tire rolls relative to the surface of the work piece, variations in surface contour cause compression of the tire structure and cause the barrier to move relative to the hub structure of the inspection device. The barrier remains in contact with the inner surface of the tire and blocks signal "cross-talk" directly through the body of liquid.

Pagano detects vertical movement of the barrier relative to the hub, and thereby establishes a basis for calculating the current distance between the ultrasonic transmitters/receivers and the surface of the work piece under inspection. More particularly, Pagano uses sound energy reflected from the barrier itself to calculate its vertical displacement relative to the wheel hub structure. Reflected sound analysis incorporating a signal taken from the sound barrier, i.e., a position calculation, accounts for the variable distance between the transmitters/receivers to detect surface and internal defects in the work piece. Thus, Pagano by signal analysis executes surface tracking, i.e., calculates the distance between the ultrasonic transmitters/receivers and the surface of the work piece, to accomplish defect gate triggering of the reflected sound energy.

U.S. Pat. No. 4,763,526 entitled ULTRANSONIC WHEEL PROBE WITH IMPROVED ACOUSTIC BARRIER issued Aug. 16, 1988 also to D. Pagano shows a similar inspection device but employs a modified method of detecting vertical displacement of the barrier relative to the wheel hub structure.

In either case, Pagano maintains by spring bias the acoustic barrier against the inner surface of the tire to eliminate cross-talk and detects vertical displacement of the barrier to calculate the varying distance between the ultrasonic transmitters/receivers and thereby perform reflected sound analysis relative to the work piece under inspection.

It would be desirable, however, to simplify the method of reflected sound energy analysis by maintaining a constant pseudo-focal point within the work piece.

SUMMARY OF THE INVENTION

A wheel-type transmit/receive ultrasonic inspection device establishes a constant length internal liquid sound path by mounting the ultrasonic transducers in fixed relation to a surface tracking structure. The resulting sensor head maintains contact with the inner surface of the tire while concurrently maintaining a fixed distance between the ultrasonic transducers and the surface of the work piece under inspection. As a result, reflected sound energy analysis becomes simplified by virtue of a constant-depth pseudo-focal point.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which:

FIG. 7A illustrates in perspective a sensor head of the wheel assembly of FIG. 4 according to a preferred embodiment of the present invention.

FIGS. 7B and 7C illustrate side and front views, respectively, including hidden line detail and a relationship to a work piece under inspection for the sensor head of FIGS. 7A and FIG. 4.

DETAILED DESCRIPTION OF THE PREFERRED EMBODIMENT

Figure 1:
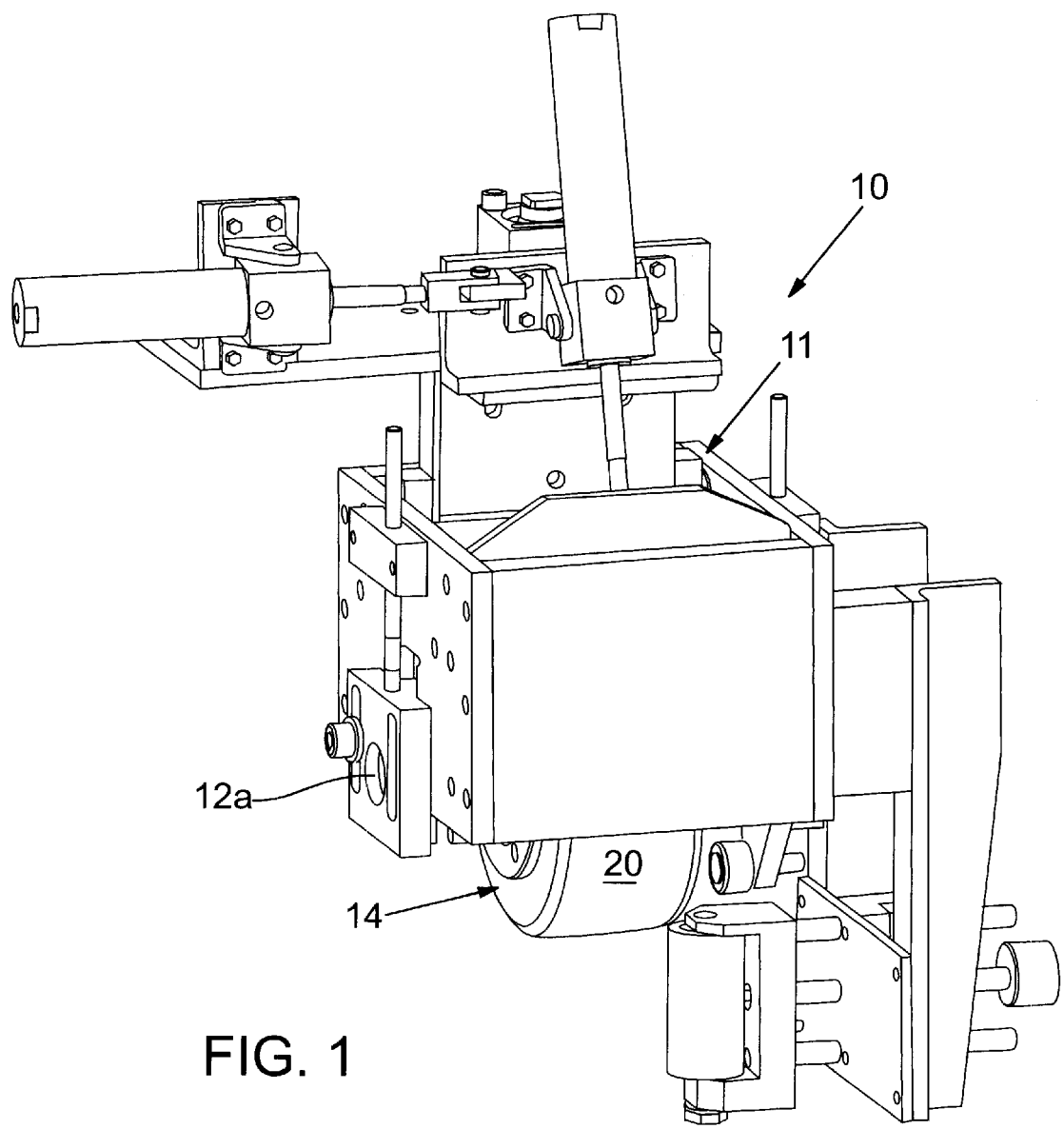
FIG. 1 illustrates in perspective a first embodiment of the present invention as applicable to the web portion of a rail work piece under inspection.
Figure 2:
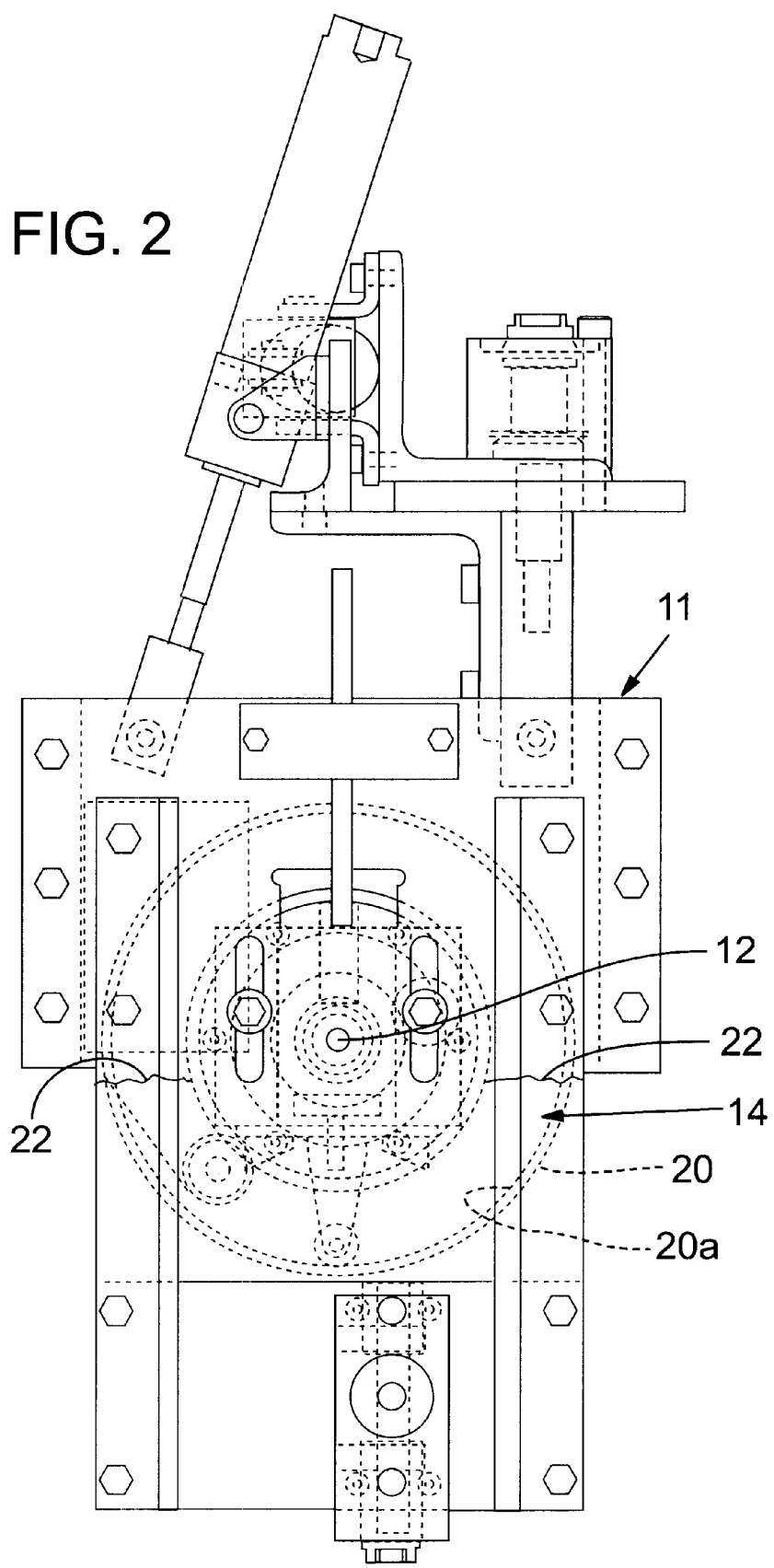
FIG. 2 illustrates a side view including hidden line detail of the wheel-type inspection device of FIG. 1.
Figure 3:
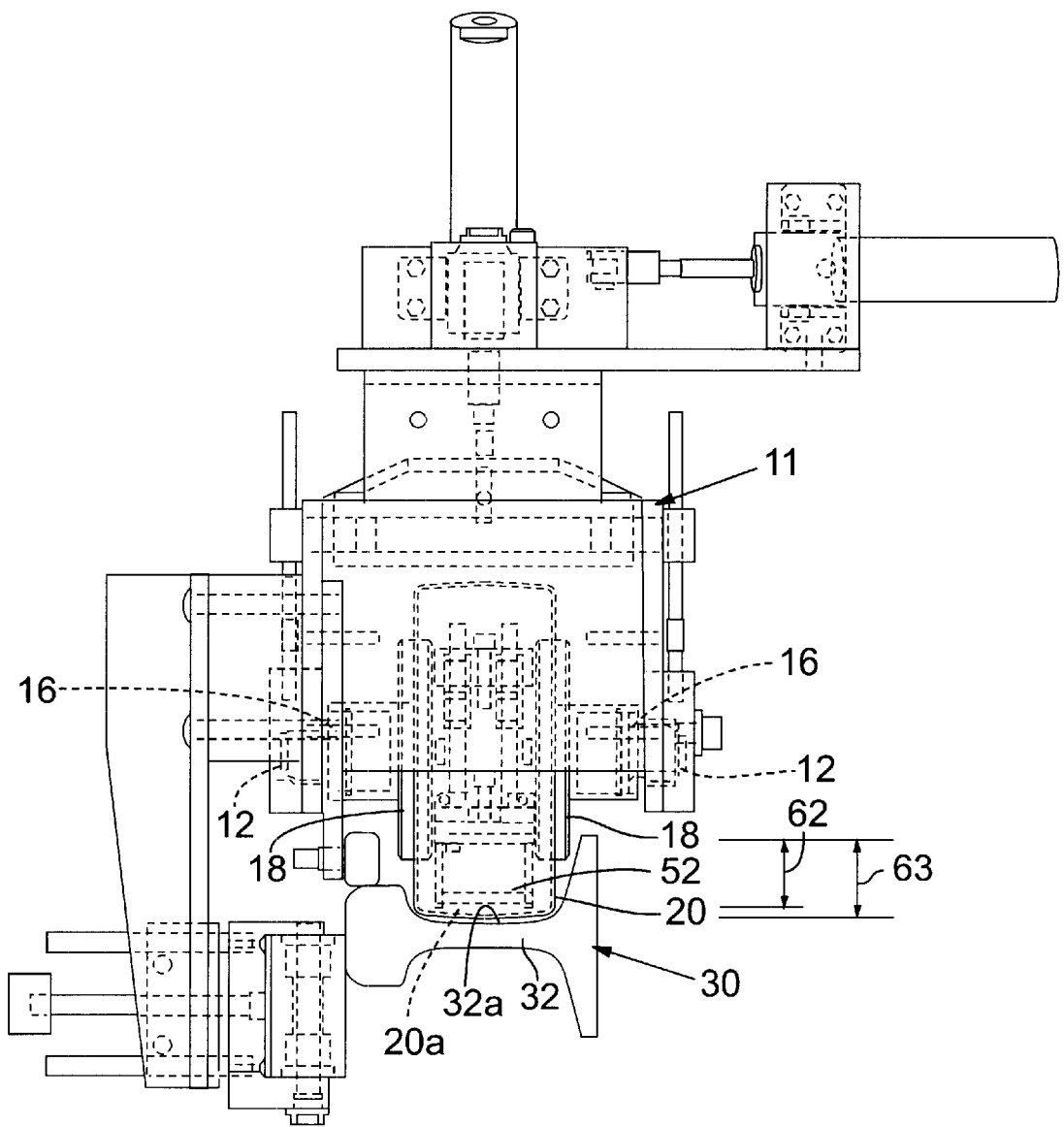
FIG. 3 illustrates a front view including hidden line detail of the wheel-type inspection device of FIG. 1.

FIGS. 1–3 illustrate a first embodiment of the present invention as applicable to the web portion 32 of a rail 30 (shown in FIG. 3). FIG. 1 illustrates device 10 in perspective and FIGS. 2 and 3 illustrate side and front views, respectively, of the embodiment of FIG. 1 illustrating by dashed line internal components thereof.

With reference to FIGS. 1–3, inspection device 10 includes a stationary frame 11 supporting a variety of structural components moveable in relation thereto. Accordingly, it will be understood that frame 11 remains stationary and a work piece, e.g., rail 30, moves therepast. For example, inspection device 10 includes a variety of positioning elements responsible for suitably positioning rail 30 relative to device 10. The objective in moving rail 30 past device 10 is to engage a wheel assembly 14 including ultrasonic transducers driving sound energy into rail 30 and collecting reflected sound energy therefrom. The following discussion will focus, therefore, on wheel assembly 14 as mounted within device 10 and its engagement of rail 30. Inspection device 10 includes a hollow and fixed, i.e., non-rotating, axle 12 about which a tire 20 rotates. Wheel assembly 14 includes left and right bearings 16, individually 16a and 16b respectively, rotatably supporting tire 20. Wheel assembly 14 includes hubs 18, individually left hub 18a and right hub 18b, as coupled to bearings 16a and 16b, respectively. Tire 20 is a deformable resilient, e.g., rubber or plastic, element and mounts about the outer peripheral annular edges 19, individually 19a and 19b, of hubs 18a and 18b, respectively.

In the particular example illustrated in FIG. 1, rail 30 moves longitudinally relative to device 10 and tire 20 contacts and rolls against the surface of web portion 32 of rail 30. Within the lower hollow space or well defined by hubs 18 and by tire 20, a body of liquid 22 resides. As described more fully hereafter, liquid 22 serves as a carrier for ultrasonic sound waves produced by device 10 and thereafter detected by device 10 in reflected form.

Figure 4:
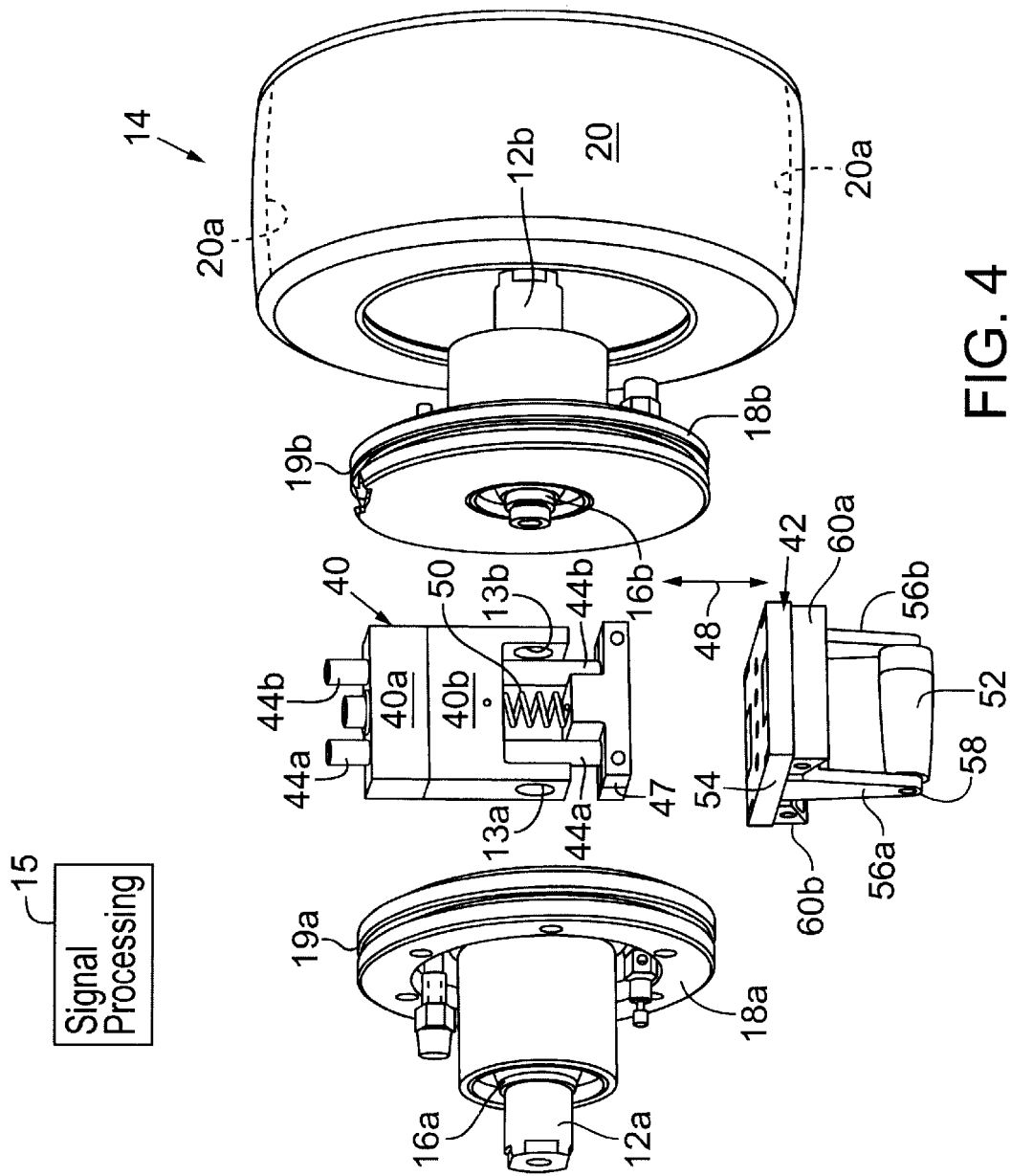
FIG. 4 illustrates in exploded perspective view a wheel assembly of the wheel-type inspection device of FIG. 1 according to a preferred embodiment of the present invention.

FIG. 4 illustrates in exploded perspective view wheel assembly 14 and its internal components including ultrasonic transmitter/receiver mounting according to a preferred embodiment of the present invention. In FIG. 4, hubs 18 are shown apart from tire 20. Components illustrated in FIG. 4 intermediate of hubs 18 mount within tire 20 during operation of device 10. Within the hollow space of wheel assembly 14, an axle block 40 mounts to fixed axle 12. Axle block 40 mounts fixedly to axle 12 and therefore remains in fixed downward-facing orientation as tire 20 rotates in relation to a work piece under inspection. A sensor head 42 also mounts within tire 20 and attaches to block 40 in downward orientation.

In the particular embodiment illustrated, axle 12 is two separate elements, a left portion 12a and right portion 12b, each affixed relative to frame 11. Each of axles 12a and 12b are hollow to allow routing of wires from within wheel assembly 14 to an external signal processing element 15. Axel block 40 mounts therebetween at its axel mount apertures 13a and 13b.

Block 40 includes a pair of upward-projecting mount rods 44, individually left mount rod 44a and right mount rod 44b. Block 40 also includes a corresponding pair of apertures 46, individually left aperture 46a and right aperture 46b. Each of rods 44 slidably engages block 40 at the corresponding one of apertures 46. The lower ends of rods 44 carry a mount block 47. As described more fully hereafter, sensor head 42 attaches to mount block 47. Sensor head 42 thereby moves vertically relative to block 40 as indicated at reference numeral 48. A bias spring 50 compresses between blocks 40 and 47 and thereby urges sensor head 42 downward and away from block 40. The distal end of sensor head 42 includes a generally cylindrical and rotatably mounted cam follower 52. More particularly, sensor head 42 includes an upper block 54 coupled via block 47 to the upward-projecting rods 44a and 44b. Extending downward from block 54, a pair of cam support plates 56, individually plates 56a and 56b, carry at their distal end a cam support axle 58. Cam follower 52 mounts rotatably upon axle 58. Bias spring 50 urges sensor head 42 downward and thereby maintains cam follower 52 against the lower inner surface 20a (not shown in FIG. 4) of tire 20.

The under surface 54a of block 54 carries ultrasonic transmitter and receiver crystals 60, individually transmit crystal 60a and receive crystal 60b. As is known in the art, a given ultrasonic transmit/receive crystal 60 may perform either a transmit or a receive function. Accordingly, reference herein to a transmit crystal 60a and to receive crystal 60b is arbitrary with respect to the particular crystals shown as either such crystal 60 may perform either the transmit or the receive function. Crystals 60 do mount, however, in fixed position relative to cam follower 52 by virtue of the rigid cam support plates 56 extending downward from block 42 and carrying at their distal end cam follower 52.

It will be appreciated, therefore, that crystals 60 remain at fixed distance relative to the lower inner surface 20a of the tire 20 that is in and around the contact between the roller 52 and surface 20a (sometimes referred to as the target area for the sound energy of the transducers 60). Thus, inspection device 10 maintains a constant length internal liquid sound path between crystals 60 and surface 32a of web 32. Accordingly, analysis of reflected sound waves taken by device 10 need not account for variation in distance between crystal 60 and surface 32a as such distance remains constant. In other words, device 10 maintains its pseudo-focal point within rail 30 at a fixed depth relative to surface 32a of rail 30. This simplifies the electronics and signal processing requirements of device 10 relative to prior wheel-type inspection devices which allow variation in distance between ultrasonic transmitters/receivers and the surface of a work piece under inspection, i.e., which allow depth-variation in the pseudo-focal point.

Figure 5:
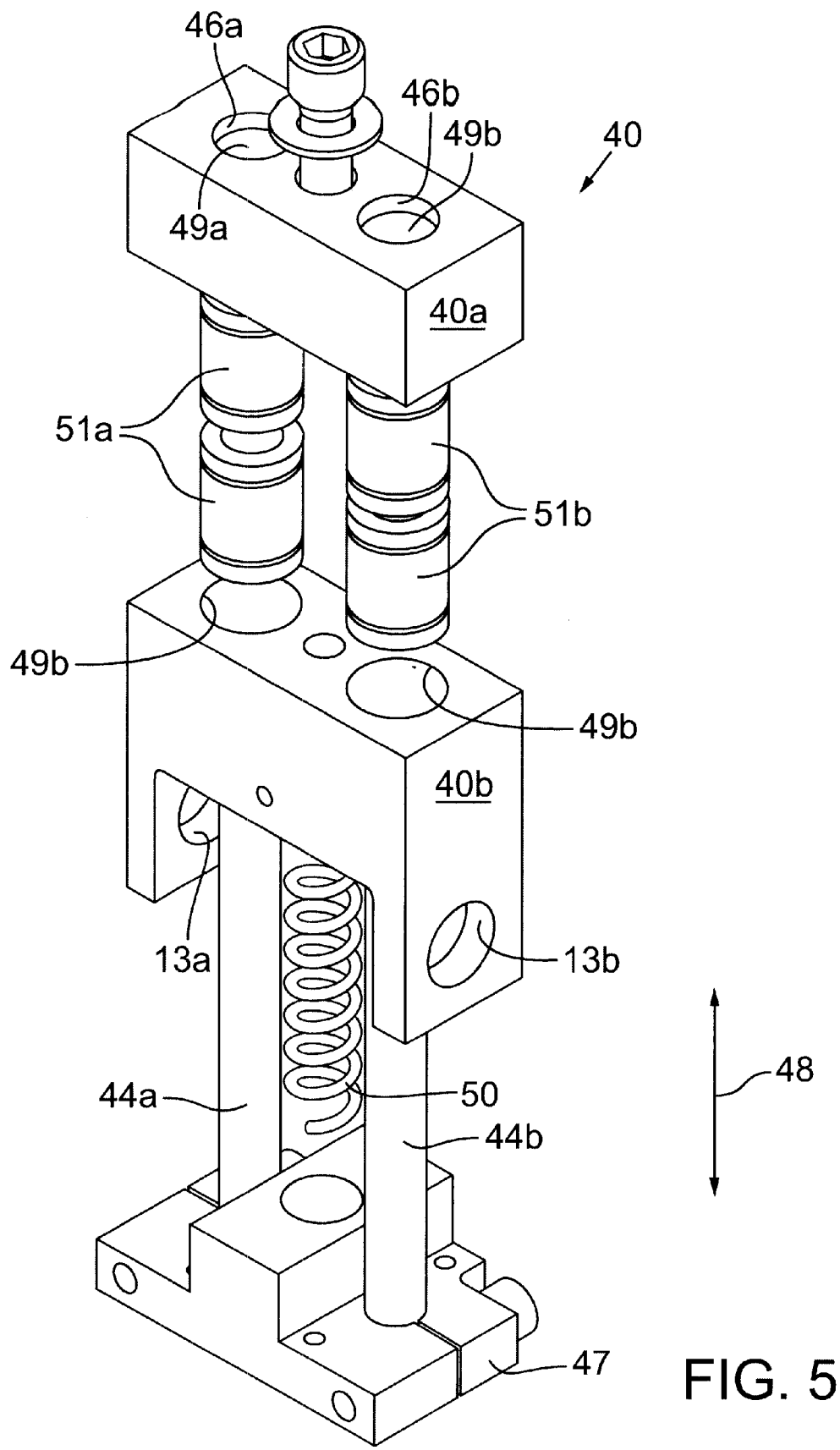
FIG. 5 illustrates in exploded perspective view an axle block of the wheel assembly of FIG. 4.
Figure 6A:
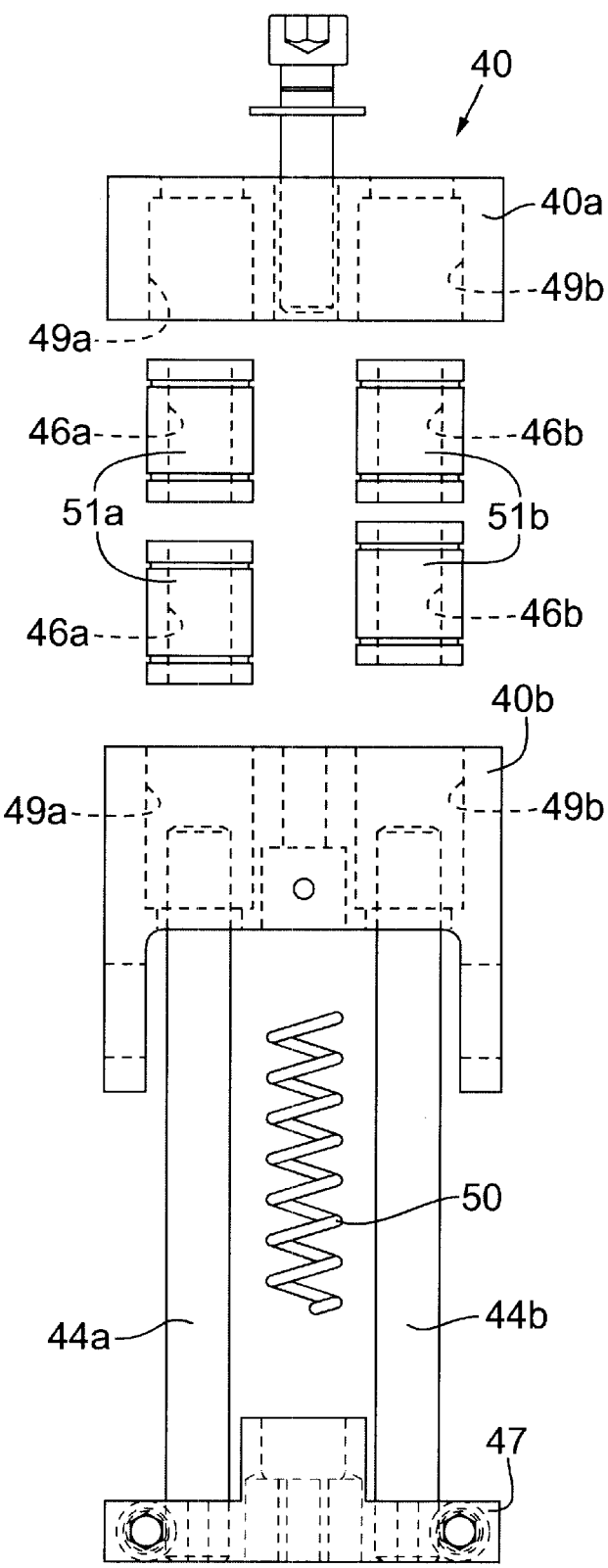
FIG. 6A illustrates in exploded front view the axle block of FIG. 5.
Figure 6B:
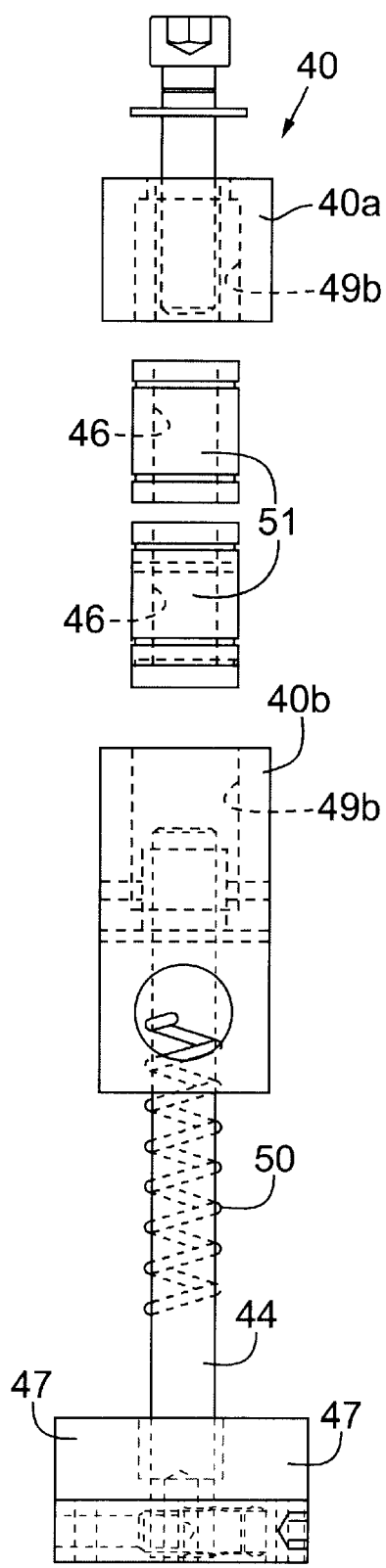
FIG. 6B illustrates in exploded side view the axle block of FIG. 5.

FIG. 5 illustrates in perspective block 40 apart from wheel assembly 14. FIGS. 6A and 6B illustrate front and side views, respectively of block 40. With reference to FIG. 5 in conjunction with FIGS. 6A and 6B, block 40 includes mount block 47 as described above including support rods 44a and 44b extending upward therefrom. Block 40 includes an upper portion 40a and a lower portion 40b. Upper portion 40a includes a pair of upper bearing mount sites 49, individually 49a and 49b, receiving therein a pair of upper linear bearings 51, individually 51a and 51b, respectively. Lower portion 40b includes a pair of lower bearing mount sites 49, individually 49a and 49b, respectively, receiving a pair of lower linear bearings 51, individually 51a and 51b. Thus, the lower linear bearings 51a and 51b mount within lower mount sites 49a and 49b of lower block 40b. The upper pair of linear bearings 51a and 51b mount within upper mount sites 49a and 49b of upper portion 40b of block 40. With linear bearings 51 captured in their respective mount sites 49, upper portion 40a and lower portion 40b join together and capture upper and lower bearings 51 in their respective upper and lower mount sites 49. Left upper bearing 51a and left lower bearing 51a align and define a mid portion of aperture 46a. Similarly, right upper bearing 51b and right lower bearing 51b align and define a mid portion of aperture 46b.

Thus, with upper portion 40a and lower portion 40b joined together and capturing thrust bearings 51 therebetween, apertures 46a and 46b of bearings 51 receive and allow vertical displacement of rods 44a and 44b. Spring 50 compresses between mount block 47 and lower portion 40b of block 40 and thereby urges block 47 downward.

FIGS. 7A–7C illustrate sensor head 42 separate from wheel assembly 14. FIG. 7A illustrates in perspective sensor head 42 while FIGS. 7B and 7C illustrate side and front views respectively, including hidden line detail. With reference to FIGS. 7A–7C, sensor head 42 includes block 54 adapted for coupling to block 47 as described above. Crystals 60a and 60b mount to the downward facing surface 54a of block 54 and thereby maintain a downward facing orientation during operation of device 10. With block 54 mounted to block 47, and with block 47 urged downward by virtue of spring 50, cam follower 52 remains in contact with the inner surface 20a of tire 20 (as best illustrated in FIGS. 7B and 7C). With the surface 32a of work piece 30 maintained in contact with tire 20, the distance 62 between crystals 60a and 60b and inner surface 20a of tire 20 remains fixed. Furthermore, the distance 63 between crystals 60 and surface 32a of rail 30 remains fixed.

As illustrated in FIG. 7C, the particular shape of cam follower 52, i.e., a lesser diameter at one end relative to the other end and a curved profile, is adapted for use against a particular work piece. In this particular embodiment, cam follower 52 is shaped in profile to match the profile of surface 32a of work piece 30. This aids in shaping tire 20 to appropriately conform to the expected contour of rail 30.

As is well understood in the art, however, variations in contour of work piece 30 result in vertical deflection of cam follower 52. Fortunately, as provided under the present invention any such vertical deflection of cam follower 52 also results in identical vertical deflection of crystals 60a and 60b. As a result, the fixed distance 62 between crystals 60 and the inner surface 20a of tire 20 simplifies analysis of reflected sound energy.

Figure 8A:
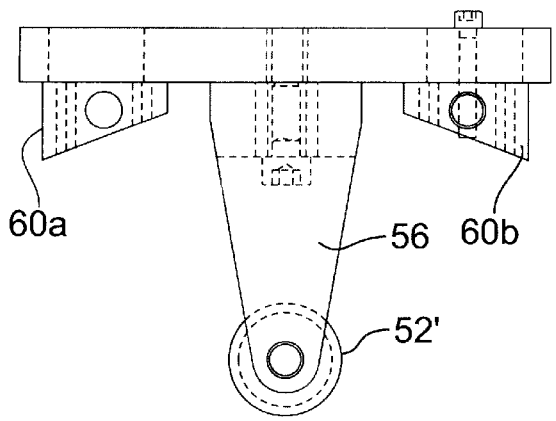
FIGS. 8A and 8B illustrate a first modified form of the sensor head of FIGS. 4 and 7A–7C.
Figure 8B:
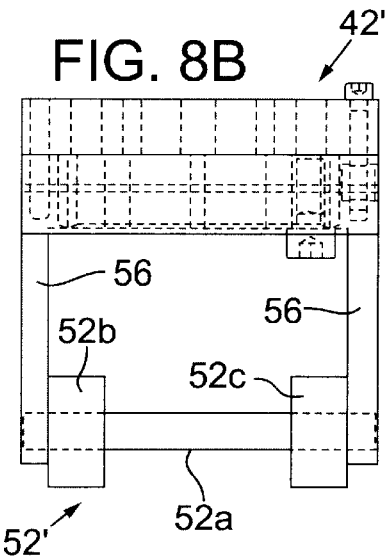

FIGS. 8A and 8B illustrate a modification of the present invention. More particularly, FIGS. 8A and 8B illustrate a first modified sensor head 42' including a modified cam follower 52'. It will be understood that modified sensor head 42' mounts and operates in fashion similar to sensor head 42 relative to device 10 as described above including a fixed distance 62 between crystals 60 and the inner surface 20a of tire 20 and therefore a fixed distance to the surface 32a of work piece 30. In FIGS. 8A and 8B, cam follower 52' includes a mid portion 52a of significantly less diameter relative to the end portions 52b and 52c. As a result, fluid 22 (not shown in FIGS. 8A and 8B) exists at surface 20a and between cam follower 52' and tire 20.

Figure 9A:
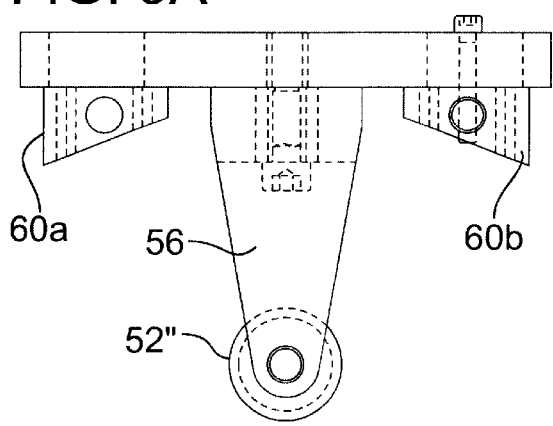
FIGS. 9A and 9B illustrate a second modified form of the sensor head of FIG. 4 and FIGS. 7A–7C.
Figure 9B:
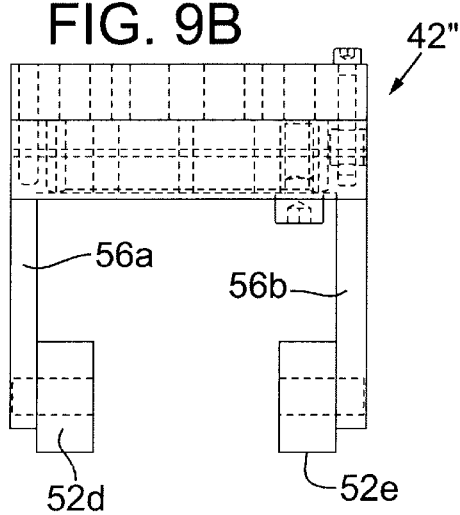

FIGS. 9A and 9B illustrate a second modified sensor head 42" including a second modified cam follower 52". In the embodiment of FIGS. 9A and 9B, cam follower 52" comprises separate cams 52d and 52e each rotatably mounted to plates 56a and 56b respectively. In this embodiment of the present invention, fluid 22 (not shown) resides throughout the region intermediate crystals 60a and 60b and the inner surface 20a (not shown) of tire 20.

Figure 10A:
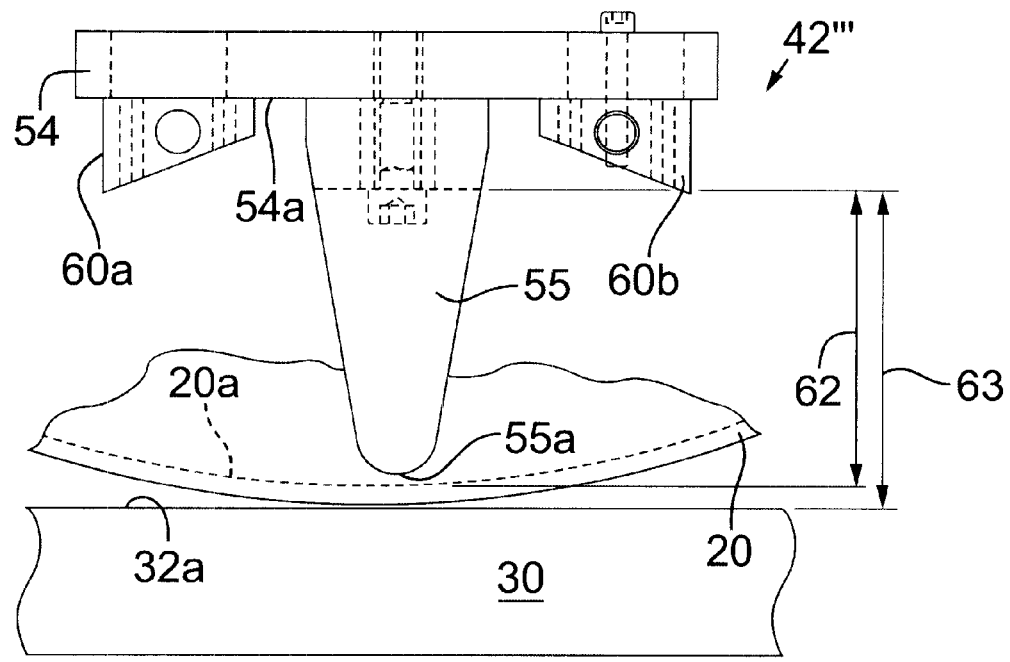
FIGS. 10A and 10B illustrate a third modified form of the sensor head of FIG. 4 and FIGS. 7A–7C including an ultrasonic acoustic barrier.
Figure 10B:
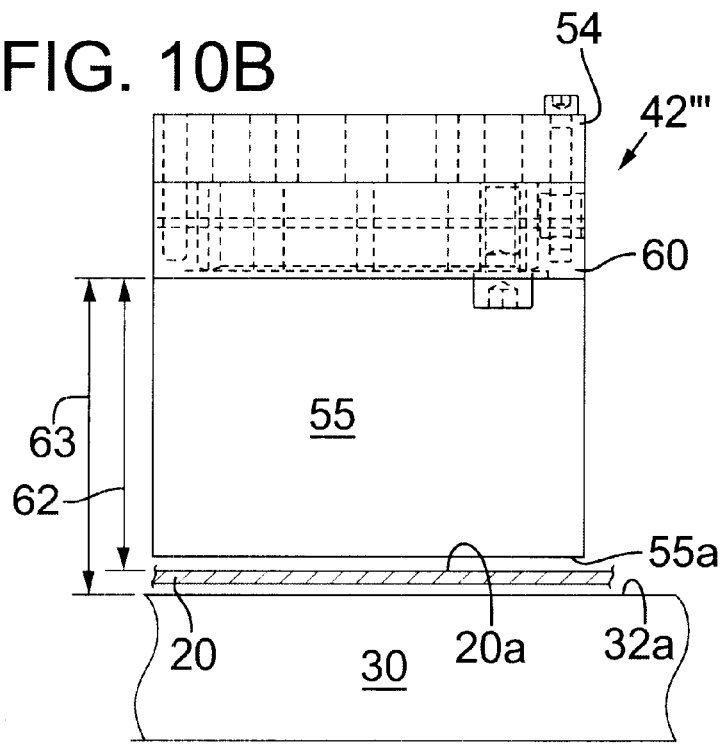

FIGS. 10A and 10B illustrate a third modified form of the present invention including a third modified sensor head 42'''. In FIGS. 10A and 10B, plates 56a and 56b as well as cam follower 52 are replaced by an acoustic barrier 55. Acoustic barrier 55 mounts to block 80 and extends downward from block 80 to engage and maintain contact with the inner surface 20a of tire 20. In this embodiment of the present invention, acoustic barrier 55 remains in contact with the inner surface 20a of tire 20 by virtue of the downward bias provided by spring 50 (not shown).

It will be understood, that in all embodiments shown herein, the fixed distance 62 remains constant between crystals 60 and the inner surface 20a of tire 20. As a result, a fixed distance 63 exists between crystals 60 and the surface 32a of work piece 30. It will be understood further that the particular profile of the cam follower 52 or the lower end 55a of acoustic barrier 55 may be shaped in profile to match that of the work piece such as is illustrated with respect to the profile of work piece 30, i.e., with respect to web 32 of work piece 30.

The fixed distance maintains a constant psudo-focal point depth and thereby allows use of a constant distance/amplitude curve under time corrected gain analysis. Without a fixed psudo-focal point depth, as under the prior art, the distance/amplitude curve must be modified dynamically as a function of the changing distance between the crystals and the work piece. Thus, under the present invention sensitivity at a given depth is constant.

The fixed distant also eliminates the need for electronic surface tracking to generate a starting point of a defect gate. More particularly, because of the fixed distance the onset of the defect gate may be established in relation to, i.e.delayed a fixed time relative to, the initial transmission of sound energy from the transmit crystal. Thus, under the present invention the defect gate need not be triggered in relation to an asynchronous event.

It will be appreciated that the present invention is not restricted to the particular embodiment that has been described and illustrated, and that variations may be made therein without departing from the scope of the invention as found in the appended claims and equivalents thereof.

What is claimed is:

1. An ultrasonic inspection device for detecting defects in a work piece comprising:
   a wheel assembly including a hollow rotatable tire structure;
   an axle block within said tire structure;
   a body of fluid within said tire structure; and
   a sensor head displaceable relative to said axle block and biased outward from said axle block whereby a distal portion thereof bears against an inner surface of said tire structure which bears against said work piece and defines a target area in and around said inner surface, said sensor head carrying thereon ultrasonic transducers for directing sound energy toward said target area, said ultrasonic transducers held in fixed, spaced relation relative to said distal portion and accordingly relative to said target area.

2. A device according to claim 1 wherein said sensor head is vertically displaceable.

3. A device according to claim 1 wherein said sensor head is biased downward toward a portion of said inner surface therebelow.

4. A device according to claim 1 wherein said distal portion comprises at least one rotatable element rotating in response to said inner surface in contact therewith and moving therepast.

5. A device according to claim 1 wherein said distal portion comprises at least two rotatable elements each rotating in response to said inner surface in contact therewith and moving therepast.

6. A device according to claim 1 wherein said body of fluid is continuous from said transducers to said inner surface at least where said distal portion surface following structure contacts said inner surface.

7. An ultrasonic inspection device comprising:

a wheel assembly including a hollow rotatable tire structure;

an axle block within said tire structure;

a body of fluid within said tire structure; and a sensor head displaceable relative to said axle block and biased outward from said axle block whereby a distal portion thereof bears against an inner surface of said tire structure, said sensor head carrying thereon ultrasonic transducers held in fixed relation relative to said distal portion surface following structure;

said distal portion comprises a panel structure maintained in contact with said inner surface and establishing an ultrasonic sound barrier within a space between said transducers and extending to said inner surface.

8. In a wheel-type ultrasonic inspection device including a wheel assembly held against a work piece under inspection and having therein a pair of ultrasonic transducers and a tire with an inner surface, an improvement comprising:

a surface tracking structure maintaining a contact thereof against said inner surface of said tire and displaceable in response to surface variations of said work piece as said work piece moves therepast, and the tire being in contact with said work piece to define a target area, said surface tracking structure carrying at a fixed spaced distance from said target area said pair of ultrasonic transducers directing sound energy at said target area.

9. An improvement according to claim 8 wherein said ultra sonic transducers comprise crystals.

10. An improvement according to claim 8 wherein said contact comprises at least one rotatable element.

11. An improvement according to claim 8 wherein said surface tracking structure is vertically displaceable.

12. An improvement according to claim 8 wherein said surface tracking structure is biased downward toward said inner surface of said tire therebelow.

13. An improvement according to claim 8 wherein said contact comprises at least one rotatable element rotating in response to said inner surface of said tire in contact therewith and moving therepast.

14. An improvement according to claim 8 wherein said contact comprises at least two rotatable elements each rotating in response to said inner surface in contact therewith and moving therepast.

15. An improvement according to claim 8 wherein a body of fluid is continuous from said transducers to said inner surface of said tire at least where said contact engages said inner surface.

16. In a wheel-type ultrasonic inspection device including a wheel assembly held against a work piece under inspection and having therein a pair of ultrasonic transducers and a tire with an inner surface, an improvement comprising:

a surface tracking structure maintaining a contact thereof against said inner surface of said tire and displaceable in response to surface variations of said work piece as said work piece moves therepast, said surface tracking structure carrying at a fixed distance from said pair of ultrasonic transducers;

said surface tracking structure comprises a panel structure maintained in contact with said inner surface and establishing an ultrasonic sound barrier within a space between said transducers and extending to said inner surface of said tire.

17. A wheel-type ultrasonic inspection device comprising:

a frame;

a hollow axle mounted to said frame;

a wheel assembly including first and second hubs rotatably mounted to said axle, a tire mounted to said first and second hubs, an axle block attached to said axle, and a sensor head coupled to said axle block to permit displacement thereof in relation to said axle block, said sensor head including a surface tracking structure maintained in contact with an inner surface of said tire and carrying thereon ultrasonic transducers maintained in fixed spaced relation to said inner surface of said tire in contact with said sensor head.

18. A device according to claim 17 wherein said sensor head is vertically displaceable.

19. A device according to claim 17 further comprising a body of fluid transmitting ultrasonic sound energy emanating from said transducers and continuous from said transducers to said inner surface of said tire at least at a point of contact with said sensor head.

20. A device according to claim 17 wherein said surface tracking structure comprises at least one of a cam follower and an ultrasonic barrier panel.

* * * * *